United States Patent
Egli et al.

(10) Patent No.: US 8,523,905 B2
(45) Date of Patent: *Sep. 3, 2013

(54) INTERVERTEBRAL STABILIZATION SYSTEM

(75) Inventors: Thomas Egli, Volketswil (CH); Emmanuel Zylber, Marseilles (FR); Michael E. Lancial, St. Louis Park, MN (US)

(73) Assignee: Zimmer GmbH, Winterthur (CH)

( * ) Notice: Subject to any disclaimer, the term of this patent is extended or adjusted under 35 U.S.C. 154(b) by 906 days.

This patent is subject to a terminal disclaimer.

(21) Appl. No.: 12/128,700

(22) Filed: May 29, 2008

(65) Prior Publication Data

US 2008/0294195 A1 Nov. 27, 2008

Related U.S. Application Data

(63) Continuation of application No. 11/570,975, filed as application No. PCT/EP2005/012580 on Nov. 24, 2005.

(30) Foreign Application Priority Data

Dec. 17, 2004 (EP) ..................................... 04030000

(51) Int. Cl.
*A61B 17/70* (2006.01)
(52) U.S. Cl.
USPC ........................................................ 606/246
(58) Field of Classification Search
USPC ... 606/246–279, 300–309; 623/17.11–17.16; 403/203, 220–228, 362, 367, 369; 23/135 R, 23/135 A, 135 K, 135 L, 135 N, 536, 537
See application file for complete search history.

(56) References Cited

U.S. PATENT DOCUMENTS

| | | | | | |
|---|---|---|---|---|---|
| 1,699,825 | A | * | 1/1929 | Waltz | 439/863 |
| 4,647,245 | A | * | 3/1987 | Konsevich | 403/228 |
| 5,375,823 | A | | 12/1994 | Navas | |
| 5,425,732 | A | * | 6/1995 | Ulrich | 606/328 |

(Continued)

FOREIGN PATENT DOCUMENTS

| EP | 0669109 | * | 8/1995 |
|---|---|---|---|
| EP | 0669109 A1 | | 8/1995 |

(Continued)

OTHER PUBLICATIONS

International Search Report, PCT/EP2050-012580, 3 pgs.

*Primary Examiner* — Pedro Philogene
*Assistant Examiner* — David Comstock
(74) *Attorney, Agent, or Firm* — Seager, Tufte & Wickhem, LLC

(57) ABSTRACT

An intervertebral stabilization system for at least three vertebrae comprising
  pedicle screws attachable to the vertebrae;
  at least one rod for the connection of at least two pedicle screws to form a rigid stiffening system; and
  at least one band which is capable of being pre-stressed in tension and which is surrounded in the implanted state of the stabilization system by at least one compressible pressure member arranged between two adjacent pedicle screws for the connection of the pedicle screws to form an elastic support system,
wherein a common pedicle screw is associated both with the stiffening system and with the support system and the band can be connected or is connected to the rod by means of a band attachment.

22 Claims, 17 Drawing Sheets

(56) References Cited

U.S. PATENT DOCUMENTS

Figure 4:
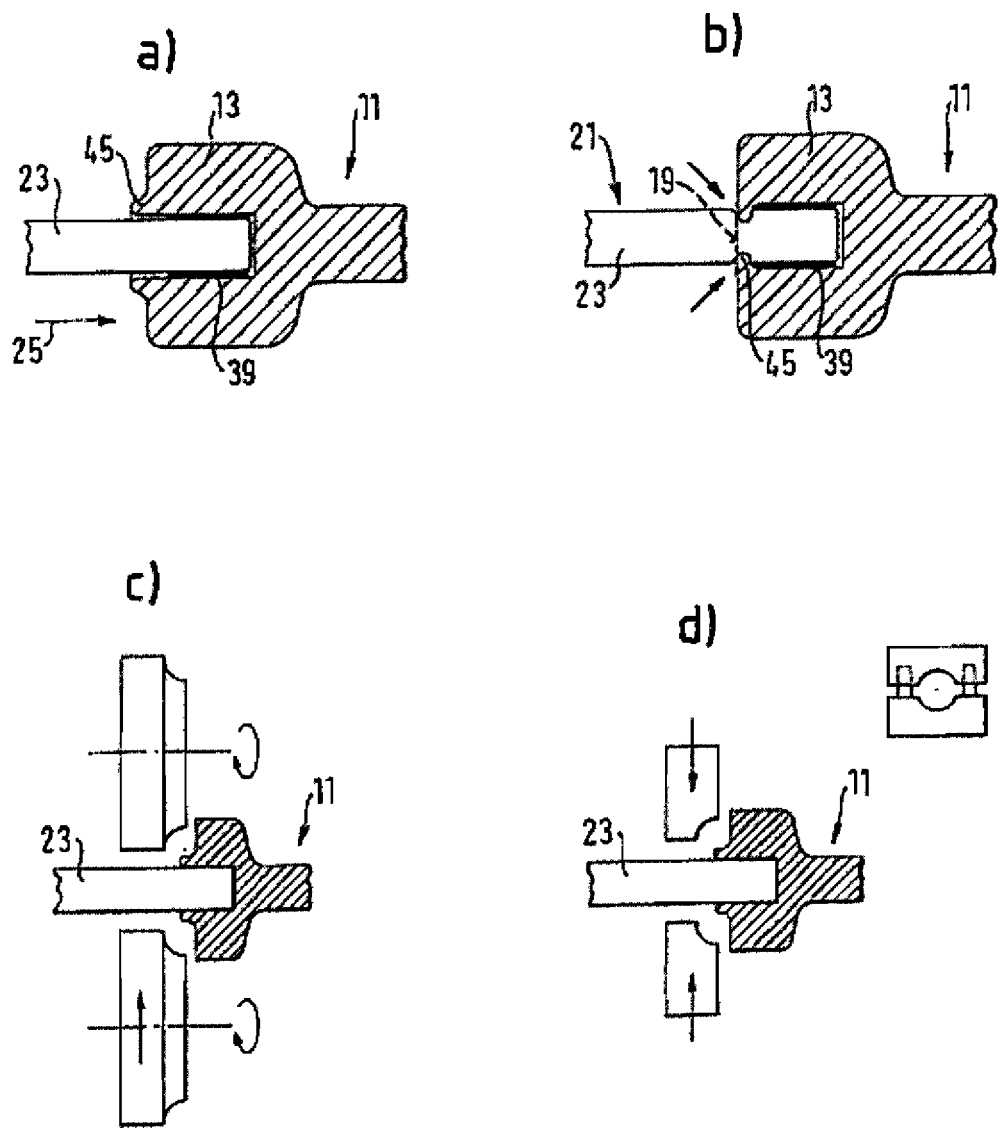

| | | |
|---|---|---|
| 5,540,688 A | 7/1996 | Navas |
| 5,562,660 A | 10/1996 | Grob |
| 5,588,190 A * | 12/1996 | Sato ............................ 24/682.1 |
| 5,611,800 A | 3/1997 | Davis et al. |
| 5,725,582 A | 3/1998 | Bevan et al. |
| 5,961,516 A | 10/1999 | Graf |
| 6,241,730 B1 | 6/2001 | Alby |
| 6,290,700 B1 | 9/2001 | Schmotzer |
| 6,669,728 B2 * | 12/2003 | Despres et al. ............ 623/16.11 |
| 6,716,213 B2 * | 4/2004 | Shitoto ........................ 606/264 |
| 6,986,771 B2 | 1/2006 | Paul et al. |
| 6,989,011 B2 | 1/2006 | Paul et al. |
| 7,326,210 B2 | 2/2008 | Jahng et al. |
| 7,686,833 B1 * | 3/2010 | Muhanna et al. ............ 606/257 |
| 2002/0035366 A1 * | 3/2002 | Walder et al. ................... 606/61 |
| 2005/0065516 A1 * | 3/2005 | Jahng ............................. 606/61 |
| 2005/0085815 A1 | 4/2005 | Harms et al. |
| 2005/0124991 A1 | 6/2005 | Jahng |
| 2005/0143737 A1 * | 6/2005 | Pafford et al. ................... 606/61 |
| 2005/0154390 A1 | 7/2005 | Biedermann et al. |
| 2005/0177157 A1 | 8/2005 | Jahng |
| 2005/0203513 A1 | 9/2005 | Jahng et al. |
| 2005/0203517 A1 | 9/2005 | Jahng et al. |
| 2005/0277926 A1 * | 12/2005 | Farris ............................. 606/61 |
| 2006/0142758 A1 | 6/2006 | Petit |
| 2006/0149238 A1 | 7/2006 | Sherman et al. |
| 2007/0016200 A1 | 1/2007 | Jackson |
| 2007/0055244 A1 | 3/2007 | Jackson |
| 2007/0129729 A1 | 6/2007 | Petit et al. |
| 2007/0198088 A1 | 8/2007 | Biedermann et al. |
| 2007/0270860 A1 | 11/2007 | Jackson |
| 2007/0293862 A1 | 12/2007 | Jackson |
| 2008/0140076 A1 | 6/2008 | Jackson |

FOREIGN PATENT DOCUMENTS

| | | |
|---|---|---|
| EP | 0669109 B1 | 5/1999 |
| EP | 1523949 A1 | 4/2005 |
| EP | 1523949 B1 | 6/2007 |
| FR | 2676911 A1 | 12/1992 |
| FR | 2715057 A1 | 7/1995 |
| FR | 2730405 A1 | 8/1996 |
| FR | 2755844 A1 | 7/2001 |
| FR | 2844180 A1 | 3/2004 |
| FR | 2867057 A1 | 9/2005 |
| NL | 7610576 A | 3/1978 |
| WO | 9417745 A1 | 8/1994 |
| WO | 9519149 A1 | 7/1995 |
| WO | WO 95/19149 * | 7/1995 |
| WO | 9905980 A1 | 2/1999 |
| WO | 9944527 A1 | 9/1999 |
| WO | 2004024011 A1 | 3/2004 |
| WO | 2005087121 A1 | 9/2005 |

* cited by examiner

Fig. 1
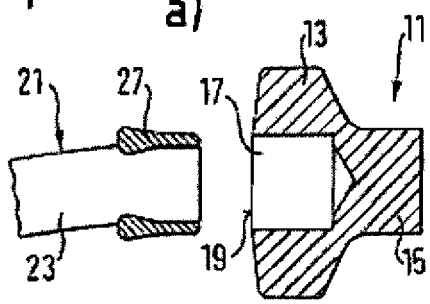
a)
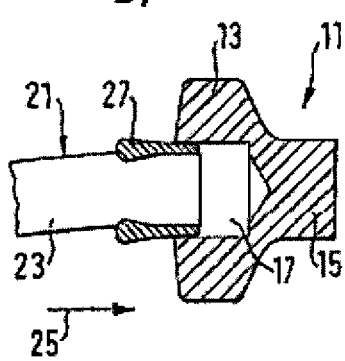
b)
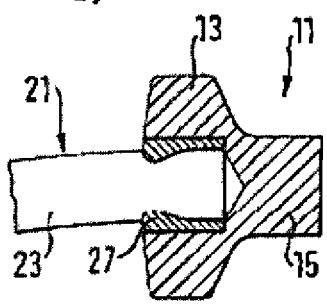
c)
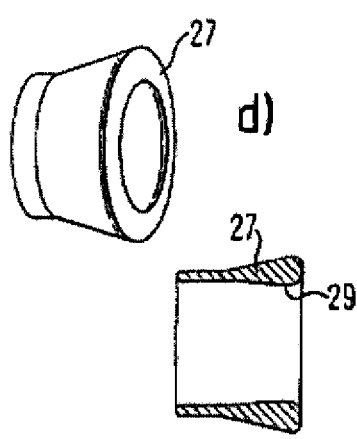
d)
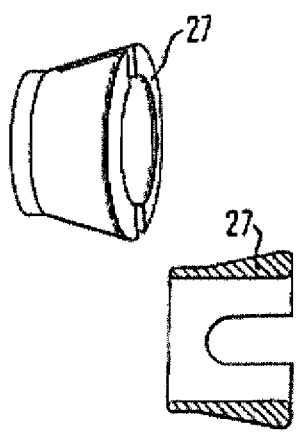
e)

Fig. 2
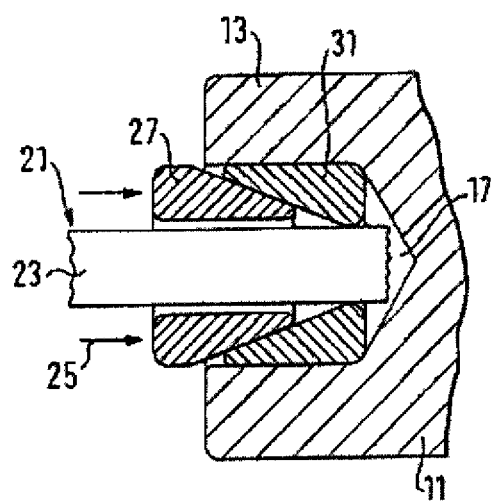
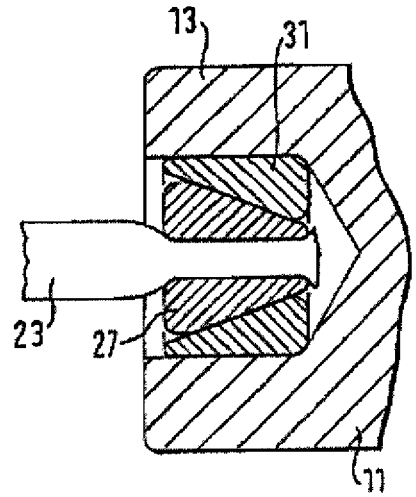
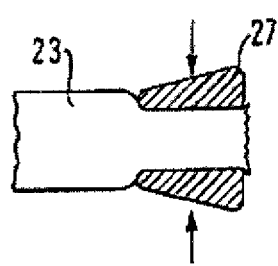
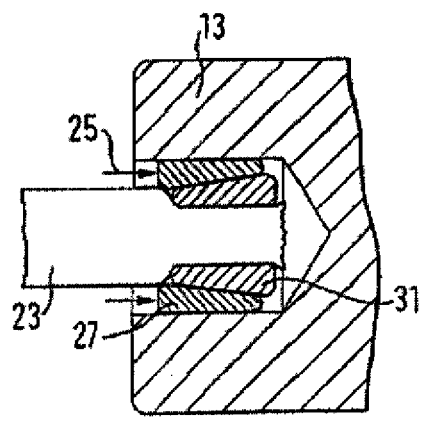

Fig. 3
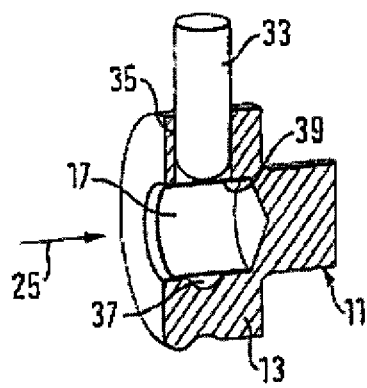 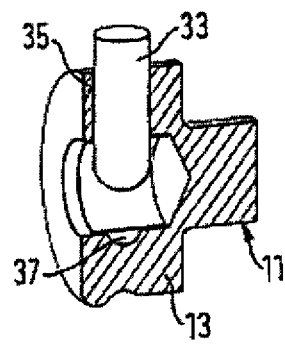
a)
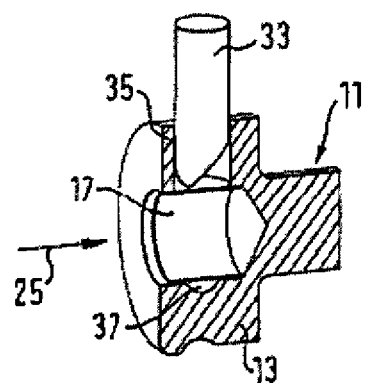 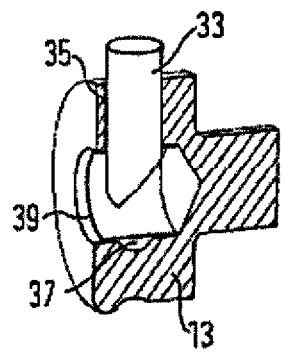
b)
c)
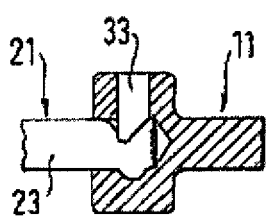 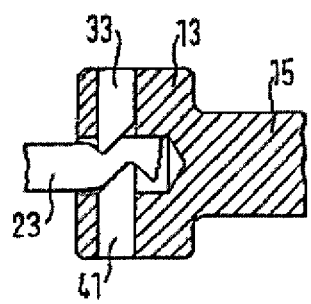 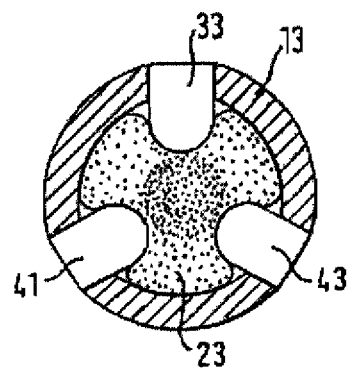

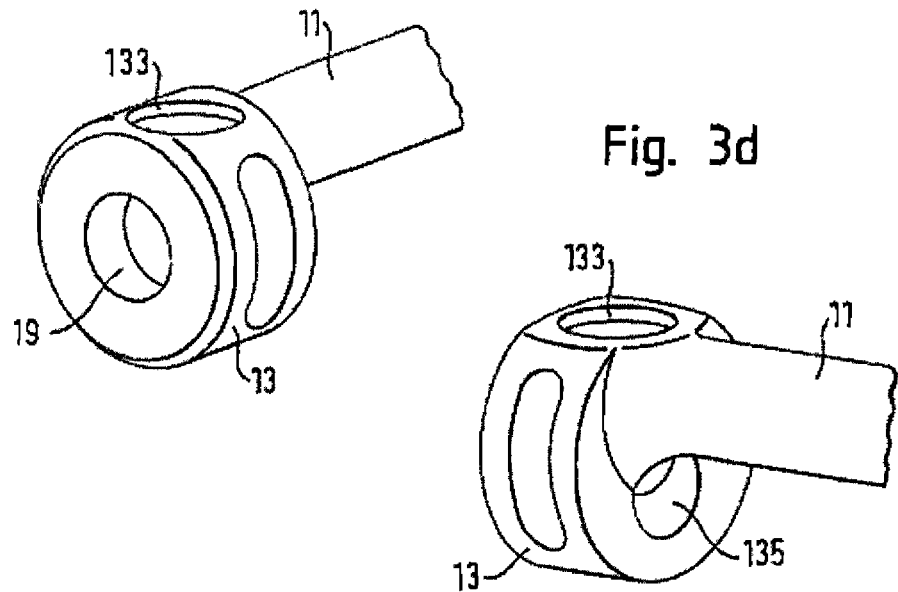
Fig. 3d
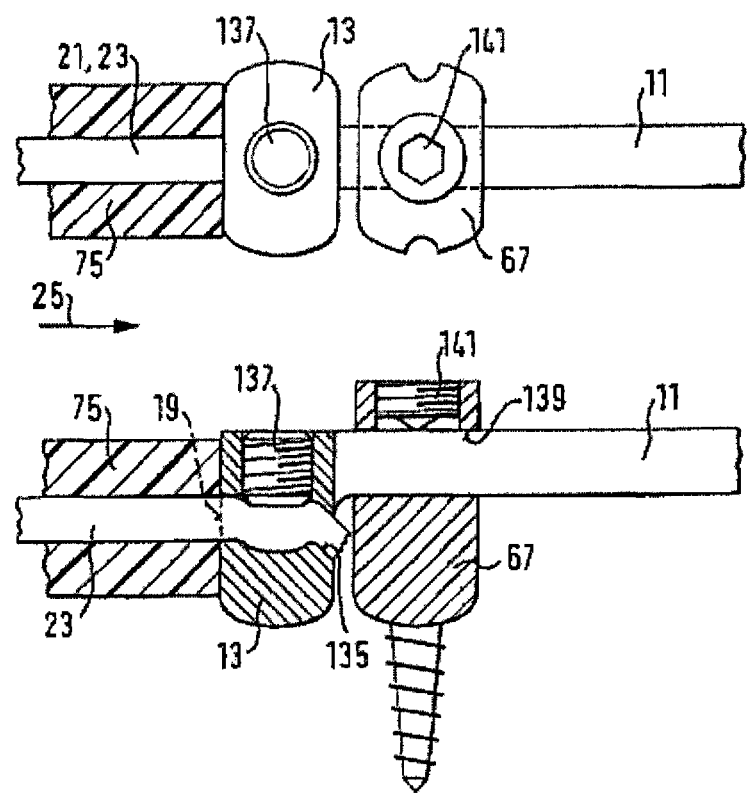

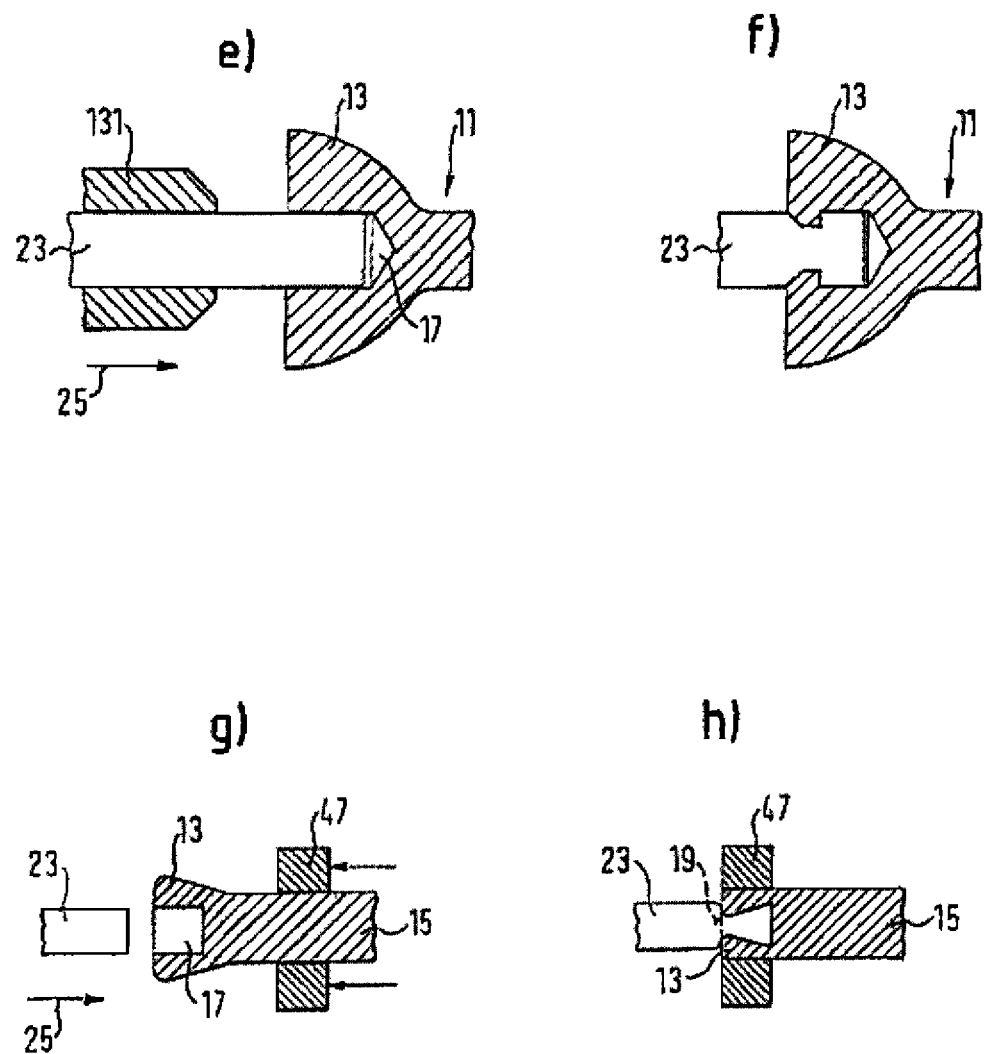

Fig. 5
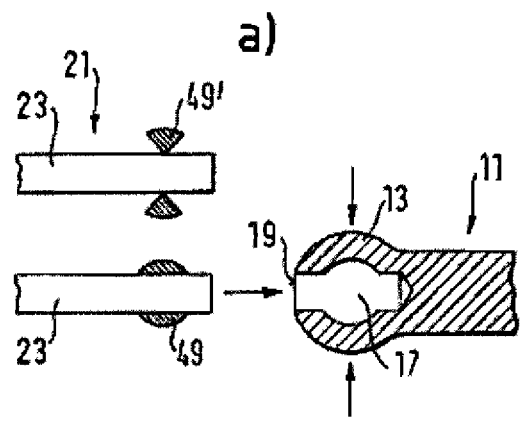
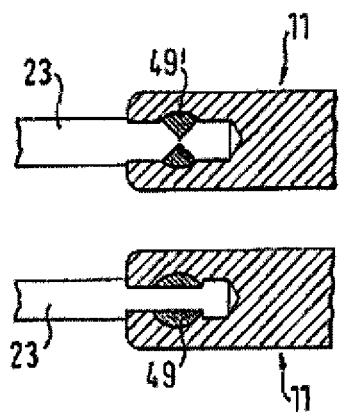

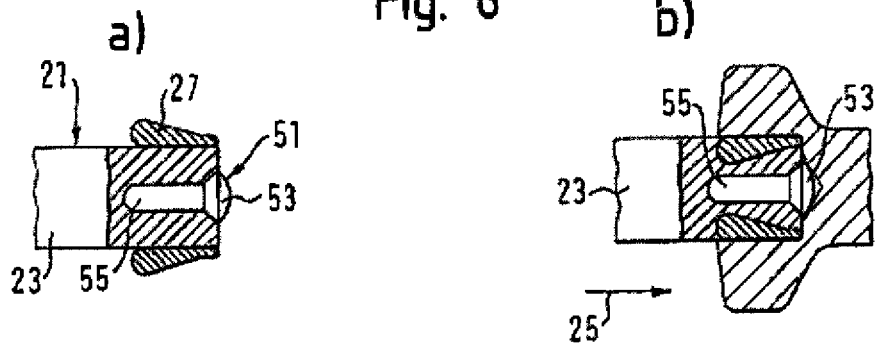
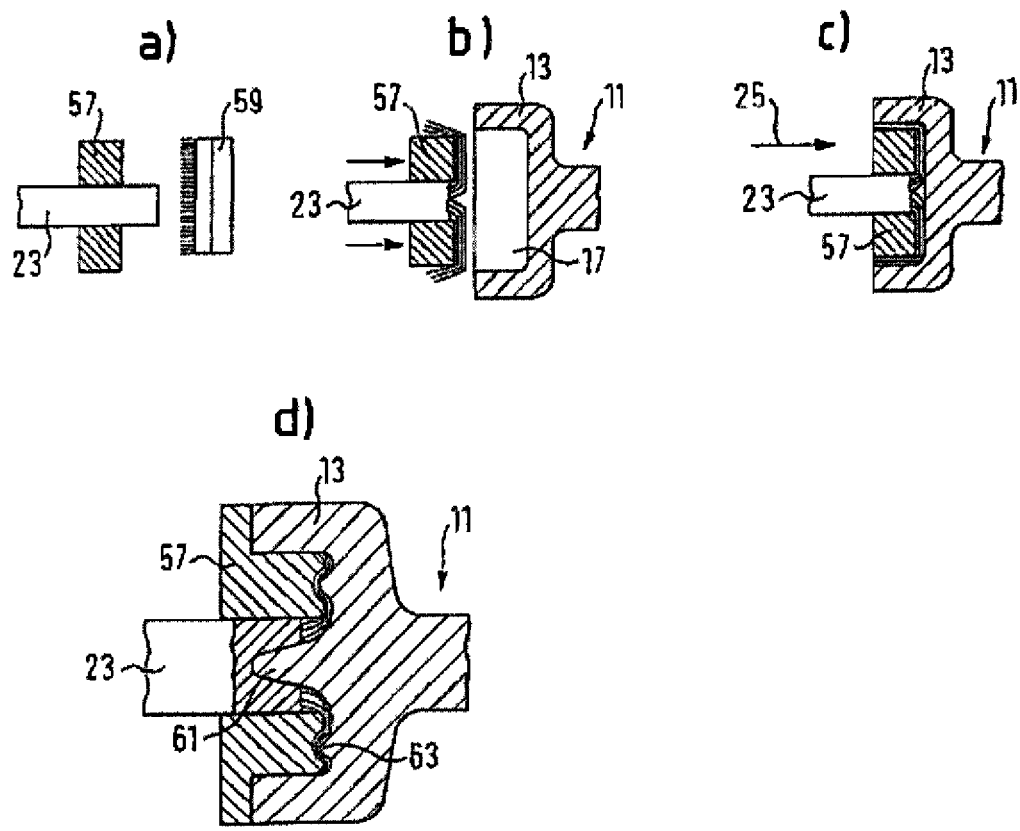

Fig. 8
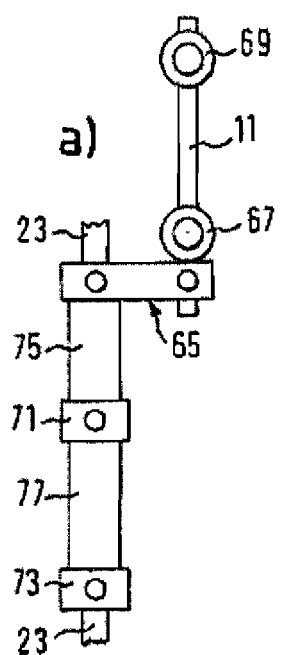
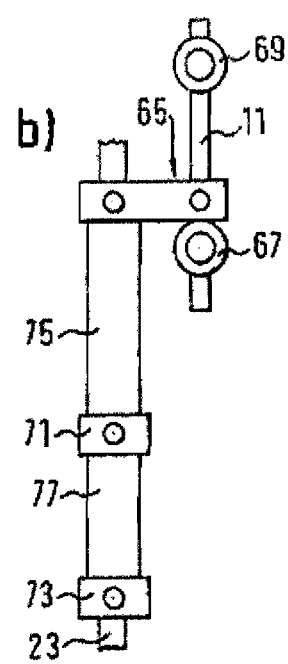
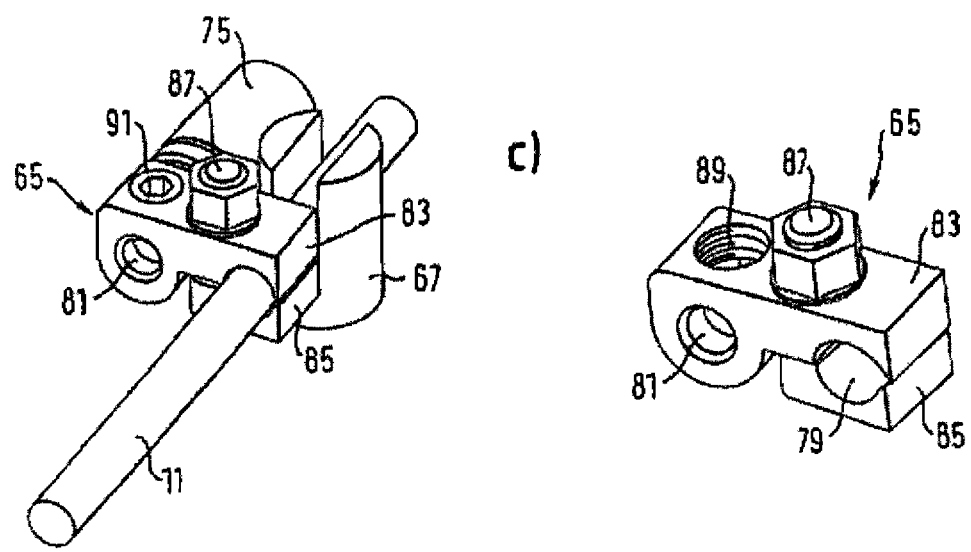

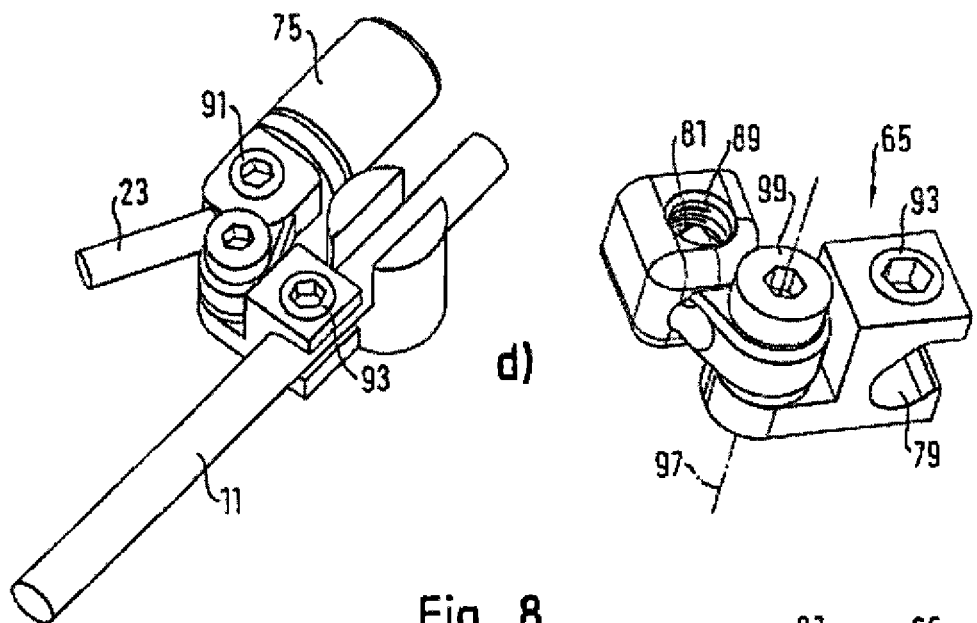
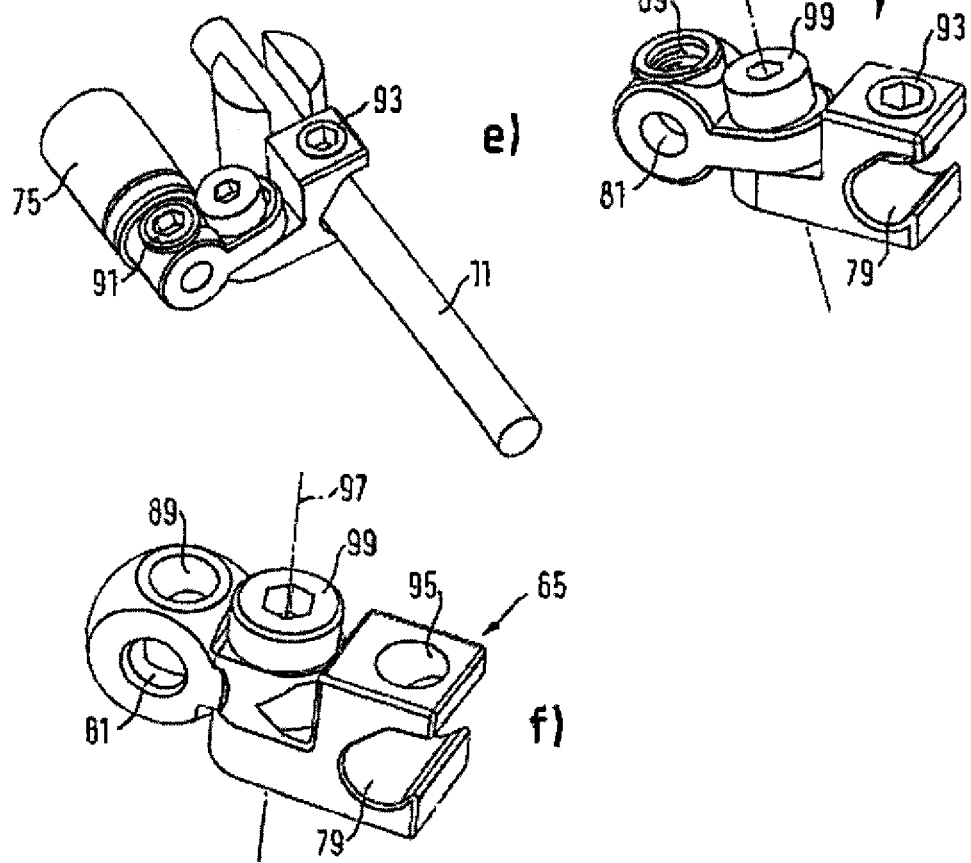
Fig. 8

Fig. 8
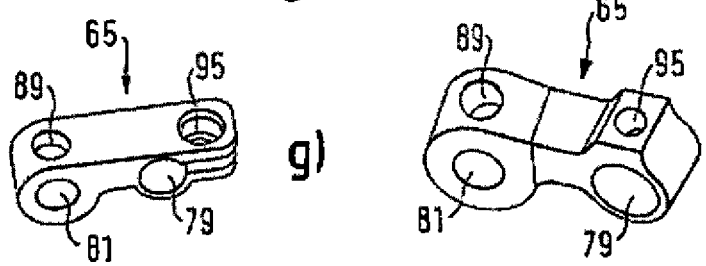
g)
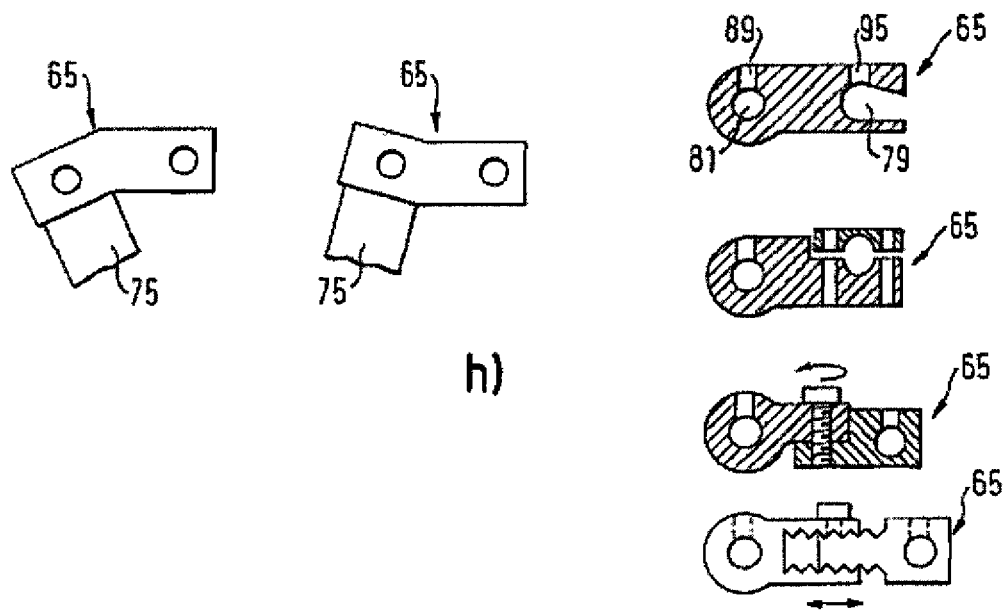
h)
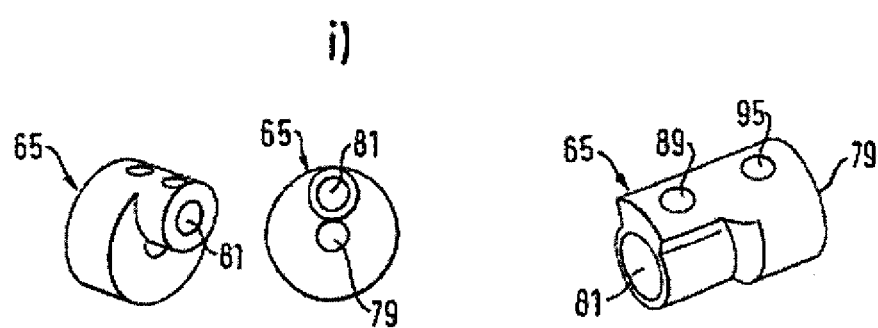
i)

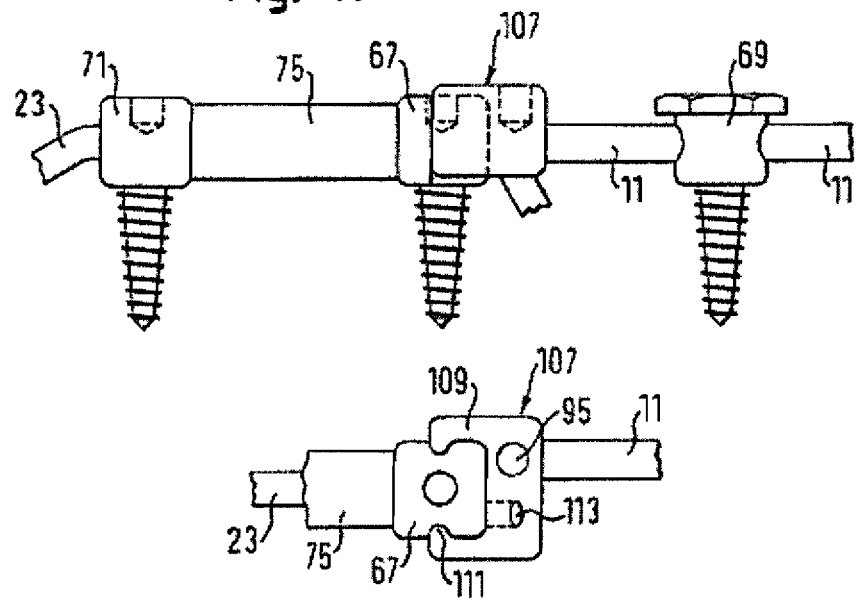
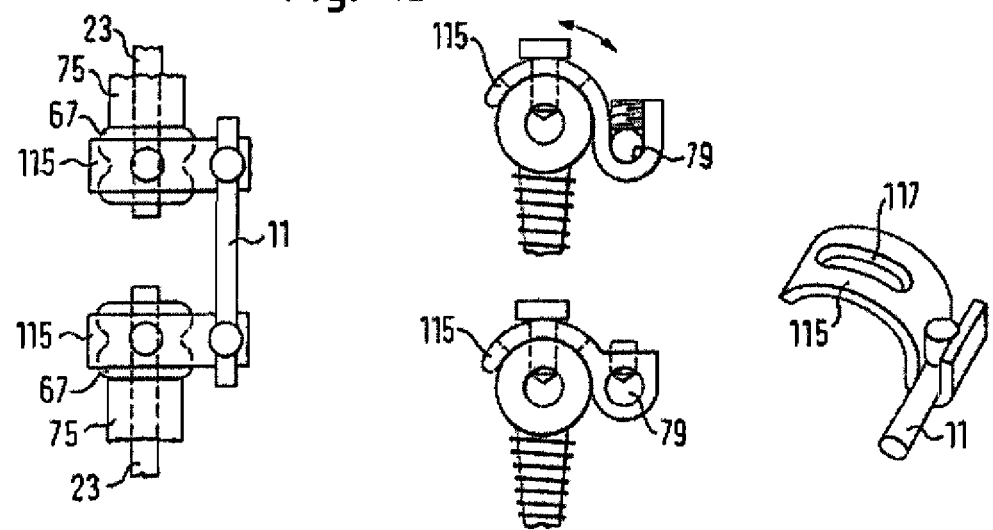

INTERVERTEBRAL STABILIZATION SYSTEM

This application is a continuation of U.S. application Ser. No. 11/570,975, filed Dec. 20, 2006; which was the 371 National Stage of International Application No. PCT/EP2005/012580, filed Nov. 24, 2005; which claims priority to European Patent Application No. 04030000.6, filed on Dec. 17, 2004, which are all incorporated herein by reference.

The invention concerns an intervertebral stabilization system for at least three vertebrae.

With deformations or degenerative changes of the vertebral column, it may be necessary to stabilize the individually affected unstable vertebral column segment by means of surgery.

In this respect, the stiffening of the affected vertebral column segment is known. With such a partial vertebral column stiffening, the intervertebral discs are at least partially removed; bony tissues are embedded between the vertebrae to be stiffened; and the vertebrae to be stiffened are connected rigidly with one another with screws and at least one rod. The stiffening of the vertebral column segment, however, makes the adjacent vertebrae more stressed with bending and stretching movements of the vertebral column than before the stiffening.

Alternatively, "with easier cases," especially before an intervertebral disc incident also appears, an implant has been more recently used which supports the affected vertebral column segment posteriorly but does not stiffen, and thus to a large extent maintains the mobility of the affected vertebrae. An elastic band with pliable spacers is thereby used between screws fastened on the vertebrae. The elastic band limits the bending movement, whereas the spacers limit the stretching movement.

The problem of the invention is to create a device of the type mentioned initially, which is designed so as to stiffen an unstable vertebral column segment in such a way that the vertebral column is stressed as little as possible with bending and stretching movements, in particular, in order to prevent further operations or at least to delay them as much as possible.

The solution of this problem takes place with the features of Claim 1, particularly in that pedicle screws which can be fastened on the vertebrae, a rod to connect at least two pedicle screws to a rigid stiffening system, and a band that can be prestressed when pulled and that, when the stabilization system is implanted, is surrounded by at least one compressible pressure body that is located between two adjacent pedicle screws and is provided to connect the pedicle screws to an elastic support system wherein a common pedicle screw is correlated both with the stiffening system and also with the support system, and the band is, or can be connected with the rod by means of a band-fastening.

The invention is consequently characterized in that the rigid stiffening system combines the known prior art, which comprises the rod, with the elastic support system, also known from the prior art, which comprises the band and the pressure body. The elastic support system, previously used as an alternative to the known rigid stiffening system is used in accordance with the invention together with the rigid stiffening system for the stabilization of an unstable vertebral column segment.

The rod of the stiffening system is designed for the stiffening of an unstable vertebral column segment comprising at least two vertebrae. The band, which is connected with the rod when the stabilization system is implanted and is or can be connected with the rod when the system is not implanted, is used to support at least one vertebra adjacent to the stiffened vertebral column segment. The rod and the band are fastened to the vertebrae to be stabilized by means of the pedicle screws.

Preferably, at least two stiffening systems, in particular, two rods, are provided, which are situated to the left and to the right of pin extensions of the affected vertebrae when the stabilization system is implemented, wherein preferably the two stiffening systems are or can be connected with one another. Furthermore, several support systems can be provided. In particular, two support systems that are connected to one end of the stiffening system can be provided for the stiffening system for each system or for several systems. Basically, several stiffening and support systems can also be provided that are alternately connected with one another in the implanted state.

In the implanted state of the stabilization system the band of the support system is prestressed when pulled. The pressure body, on the other hand, is in a compressed state—that is, it is prestressed with pressure. The rod and the band are thereby connected with one another via a band-fastening—that is, the band is fastened to the rod or vice-versa. The common pedicle screw, on which or in whose vicinity the connection of the band with the rod is usually designed in the implanted state of the stabilization system, is equally used by the rigid stiffening system and the elastic support system. If the band-fastening is located approximately in the middle between two pedicle screws, an arbitrary one of the two pedicle screws can be regarded as the common pedicle screw.

By means of the elastic support system that follows it as an extension of the rigid stiffening system, or by means of the elastic support systems that follow it on both sides of the rigid stiffening system, the vertebra(e), following the vertebrae connected rigidly with one another by the stiffening system are supported, so that these adjacent vertebrae are not exposed to increased stresses with bending and stretching movements of the vertebral column.

Advantageous embodiments of the invention are also indicated in the subclaims, the description, and the drawing.

Preferably, the band-fastening is designed as a clamping device for the clamping of the band. By means of the clamping forces of the band-fastening designed as a clamping device, it is possible to hold the band, which is under traction in the implanted state of the stabilization system, in a particularly safe and reliable manner.

It is also preferred for the band-fastening to comprise an end of the rod, a separate component, and/or the common pedicle screw.

Figure 9:
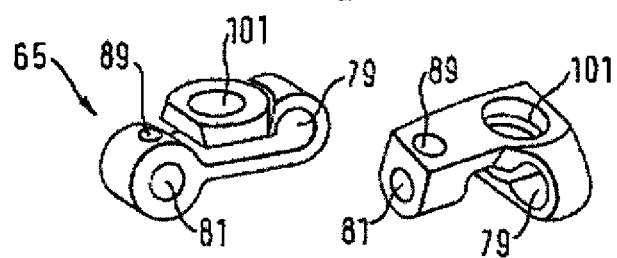
Figure 10:
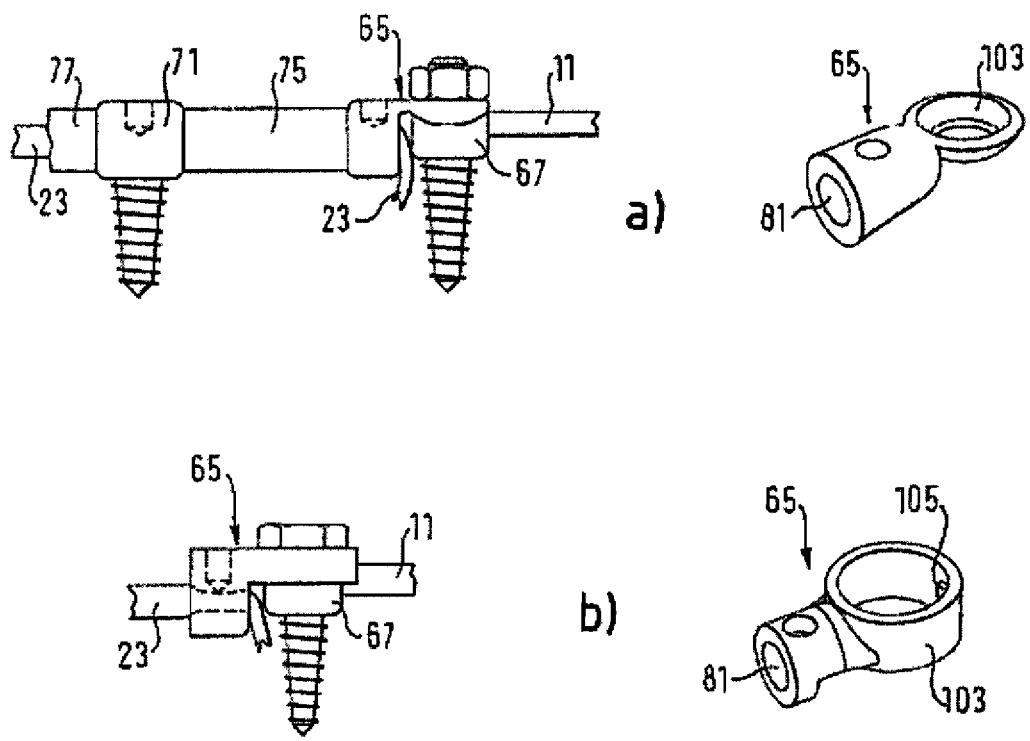

The invention is described below, as an example, with reference to the drawing, which comprises various embodiments, the individual features of which—to the extent that it makes sense—can be combined arbitrarily with one another. The figures show the following:

FIGS. 1 to 7, band-fastenings of a stabilization system in accordance with the invention that embrace an end of the rod;

FIGS. 8 to 10, band-fastenings of a stabilization system in accordance with the invention that embrace a separate component; and FIGS. 11 to 15, band-fastenings of a stabilization system in accordance with the invention that embrace a common pedicle screw.

The embodiments explained below show only the part of the stabilization system which is needed for the description of the connection between the rod of the stiffening system and the band of the support system. The same components of the different embodiments of the invention, or those components which correspond to one another, are designated with the same reference symbols.

FIG. 1 shows a stabilization system in accordance with a first embodiment of the invention with a rigid metal rod 11 of a rigid stiffening system, which is otherwise not depicted, wherein the rod 11 has an end 13, which has a larger diameter than the middle part 15 of the rod 11. The end of the rod 11, which is designed as the head 13 and which can be used, simultaneously, as the stop for an undepicted pressure body, is at least part of a band-fastening and has an essentially cylindrical hollow space 17, into which, via a band entry opening 19, an end 21 of an elastic band 23, made of plastic, for example, of an otherwise not undepicted elastic support system is introduced or can be introduced.

The band-fastening also comprises a sleeve-like clamping element 27, which is (FIG. 1c) or can be (FIG. 1a) introduced into the cavity 17 along the introduction direction 25 of the end 21 of the band 23 and is closed in the circumferential direction; the clamping element is pushed to the end 21 of the band 23 and is designed to clamp the end 21 of the band 23 with the head 13 of the rod 11, introduced into the cavity 17 of the rod 11. The sleeve-like clamping element 27 can also be designated as a clamping sleeve or as a clamping ring.

The clamping sleeve 27 is designed so that it tapers conically on its outside when it has not been introduced into the cavity 17 of the rod 11, wherein the wall thickness of the clamping sleeve 27 increases toward the end that has the larger outside diameter. In accordance with FIG. 1d, a protrusion 29, which runs along the circumference, is directed inwards and constricts the inside diameter of the clamping sleeve 27, can be designed on the inside of the clamping sleeve 27 on the end which has the larger outside diameter. In accordance with FIG. 1e, the clamping element 27 can be slit, in particular, on two opposite sides. Basically, the clamping sleeve can have a protrusion and can also be slit.

FIGS. 1a to 1c show the connection of the rod 11 with the band 23. First, the clamping sleeve 27 is pushed onto the end 21 of the band 23 that is to be introduced in the cavity 17 or rod 11 in such a way that the end of the conical clamping sleeve 27 that has the larger outside diameter faces the middle of the band 23 (FIG. 1a). Afterwards, the end 21 of the band 23, which is provided with the clamping sleeve 25 [sic; 27] is pressed into the cavity 17 of the head 13 of the rod 11 by means of a suitable tool, along the introduction direction 25 (FIG. 1b).

The end of the clamping sleeve 27 that has the larger outside diameter is compressed onto the inside diameter of the cylindrical cavity 17 of the rod 11, which at least essentially corresponds to the smaller outside diameter of the other end of the clamping sleeve 27. When assembled (FIG. 1c), the inside diameter of the clamping sleeve 27 decreases toward the end which originally has a larger outside diameter, because of the wall thickness of the clamping sleeve 27, which increases in this direction—that is, the passage of the clamping sleeve 27 is constricted in the direction of the band entry opening 19 of the cavity 17 of the head 13 of the rod 11, so that the band 23 is effectively clamped.

The clamping force of the band-fastening can be additionally reinforced by the protrusion 29 shown in FIG. 1d. A slit clamping sleeve 27 (FIG. 1e) offers the advantage that, upon introduction of the clamping sleeve 27 into the cavity 17 of the head 13 of the rod 11, additional space for material deformation is available, so that the pressing-in process can be carried out with an overall smaller expenditure of force.

FIG. 2 shows a stabilization system in accordance with a second embodiment of the invention. In contrast to the embodiment in FIG. 1, the band-fastening in accordance with FIG. 2 comprises two clamping sleeves 27, 31 braced against one another.

Analogous to FIG. 1, the first clamping sleeve 27 is shoved onto the end 21 of the band 23 to be introduced into the cavity 17 of the rod 11 in the embodiment example according to FIGS. 2a and 2b in such a way that the end of the conical first clamping sleeve 27, which has the larger outside diameter, faces the middle of the band 23 (FIG. 2a). The second clamping sleeve 31, which is used as the conical pressing ring, is, in a minor image to the first clamping sleeve 27 and relative to a plane which is perpendicular to the introduction direction 25, pressed into the cavity 17 of the head 13 of the rod 11 (FIG. 2a). To connect the band 23 with the rod 11, the first clamping sleeve 27 is pressed along the introduction direction 25 into the cavity 17 of the head 13 of the rod 11, wherein the first clamping sleeve 27 is braced with the second clamping sleeve 31.

The first clamping sleeve 27 is deformed in such a way that the band 23 is effectively clamped in (FIG. 2b). Basically, several conical pressing rings can also be provided.

In the embodiment example in accordance with FIGS. 2c and 2d, the two clamping sleeves 27, 31 are exchanged with respect to their orientations in comparison to the embodiment example according to FIGS. 2a and 2b, wherein the first clamping sleeve 27 is pressed onto the end 21 of the band 23 in the unintroduced state (FIG. 2c). When assembled, the end 21 of the band 23, provided with the first clamping sleeve 27, is introduced along the introduction direction 25 into the cavity 17 of the head 13 of the rod 11. Subsequently the second clamping sleeve 31 is pressed into the cavity along the introduction direction (FIG. 2d).

FIG. 3 shows the stabilization system in accordance with a third embodiment of the invention.

The band-fastening of the embodiment example in accordance with FIGS. 3a to 3c comprises a clamping pin 33 that can be introduced under press fit into the cavity 17 transverse to the introduction direction 25 of the end 21 of the band 23; the pin is designed to clamp the end of the band, which can be introduced into the cavity 17 of the rod 11 with the head 13 of the rod 11. The clamping pin 33 introduced through an opening 35 into the cavity 17 of the rod 11 can be designed round (FIG. 3a) or wedge-shaped (FIG. 3b) at its tip, which tip acts with radial pressure on the introduced end 21 of the band 23 relative to its longitudinal extension. A greater contact pressure on the clamped-in band 33 can be attained with a wedge-shaped clamping pin 33.

Diametrically opposite the opening 35 through which the clamping pin 33 is introduced into the cavity 17, a cavity 17 is formed on the inside of the head 13 of the rod 11, which limits the cavity 17; the pressed-in clamping pin 33 is pressed into the hollow. The clamping force on the band 23 can be increased additionally by the deviation of the band 23 created in this way. In order to facilitate the introduction of the band 23, an introduction aid designed as a sleeve 39 can be stuck on the end 21 of the band 23 to be introduced (FIGS. 3a and 3b). As can be seen in FIG. 3c, one, two, three, or any number of clamping pins 33, 41, 43 can be provided.

In the embodiment example in accordance with FIG. 3d, the band-fastening comprises a pressure element, for example, a clamping screw 137 that can be introduced into the cavity of the head 13 of the rod 11 via an opening 133 transverse to the introduction direction 25, and is designed for the clamping of the end 21 of the band 23 within the head 13 of the rod 11. Furthermore, a band exit opening 135 lying deeper and opposite the band entry opening 19 is provided, and through it the end 21 of the band 23 can again be moved out or is moved out of the cavity of the rod 11. The part of the band 23 that is not introduced into the head 13 is surrounded by a pressure body 75 that can also be designated as a cushion. The rod 11 is or can be placed into a recess 139 of a common pedicle screw 67 that is formed tuning fork-like on its upper end in the assembled state and by means of a clamping screw 141 is or can be fastened to it. The upper end of the common pedicle screw 67 can also be designed as a passage, however.

FIG. 4 shows a stabilization system according to a fourth embodiment of the invention in which the cavity 17 is constricted toward the band entry opening 19 of the head 13 of the rod 11. The constriction is thereby formed with the end 21 of the band 23 introduced into the cavity 17 by reshaping the head 13 of the rod 11. By the constriction, the band 23 is effectively clamped (FIGS. 4b, 4f, and 4h). Analogous to FIG. 3, it is also possible to use a sleeve 39 as an introduction aid for the end 21 of the band 23 in the embodiment according to FIG. 4 also, as is shown in FIGS. 4a and 4b.

In the embodiment example according to FIGS. 4a and 4b, the head 13 of the rod 11 exhibits a projection 45 that juts out against the introduction direction 25 and runs along the circumference of the rod 11. The reshaping of the projection 45 from the position shown in FIG. 4a to the position shown in FIG. 4b, in which the orientation of the projection 45 is rotated, as it were, by 90°, can be attained, for example, by roll-pressing (FIG. 4c) or by using two half-shells (FIG. 4d).

In the embodiment example according to FIGS. 4e and 4f, the head 13 of the rod 11 does not have a projection before the reshaping. Rather, when pressing in the end 21 of the introduction end 21 of the band 23, the area of the head 13 of the rod 11 forming the limit of the band entry opening 19 is deformed by means of a punch 131 in such a way, in particular, pressed inwards so that the cavity 17 to the band entry opening 19 of the head 13 of the rod 11 is constricted.

The embodiment example according to FIGS. 4g and 4h is characterized in that, before the reshaping the outside diameter of head 13 of the rod 11 and the related wall thickness of the head 13 in the area of the cavity 17 increase in the direction opposite the introduction direction 25 of the band 23. With the reshaping of the head 13 of the rod 11, a press ring 47 having an inside diameter that essentially corresponds to the outside diameter of the middle part 15 of the rod 11 moves against the introduction direction 25. The head 13 of the rod 11 is thereby compressed to the inside diameter of the press ring 47 so that the cavity 17 is constricted toward the band entry opening 19 of the head 13 because of the wall thickness of the head 13, which increases in this direction.

FIG. 5 shows a stabilization system according to a fifth embodiment of the invention in which the connection of the band 23 with the rod 11 is brought about by the reshaping of the head 13 of the rod 11. The head 13 of the rod 11 and the cavity 17 within the head 13 are shaped spherically, at least before the reshaping, wherein the diameter of the band entry opening 19 is smaller than the cavity 17 formed in the head 13. The cavity 17 is thus already constricted before the reshaping for the band entry opening 19.

To bring about the connection of the band 23 with the rod 11, a ring 49, in particular a tapered ring 49', is first shoved onto the end 21 of the band 23 (FIG. 5a). The end 21 of the band 23, provided with the ring 49, 49', is then introduced into the cavity 17 of the head 13 of the rod 11, wherein the head 13 of the rod 11 and thus also the ring 49, 49' is compressed so that the band 23 is effectively clamped (FIG. 5b). It is possible to additionally increase the pressing force exerted on the band 23 by tapering the ring 49'.

FIG. 6 shows a stabilization system according to a sixth embodiment of the invention. The embodiment according to FIG. 6 essentially corresponds to the embodiment according to FIG. 1, with the difference that the band-fastening also comprises an inlay 51, made, in particular, of metal or plastic, which is worked into the end 21 of the band 23, in particular, centrically, which can be (FIG. 6a) or is (FIG. 6b) introduced into the cavity of the rod 11 and which extends along the introduction direction 25 of the band 23.

The inlay 51 is designed in the shape of a pin and comprises a head 53 and a shaft 55, wherein the diameter of the head 53 is larger than that of the shaft 55. The head 53 protrudes, in part, from the end 21 of the band 23. By means of the inlay 51, it is possible to increase the pressing pressure, exerted on the clamped-in band 23, and thus the holding force of the connection between the band 23 and the rod 11, brought about by the band-fastening.

FIG. 7 shows a stabilization system according to a seventh embodiment of the invention. In FIG. 7, the band 23 is widened to form a large number of strength carriers, in particular, fibers of the band 23, and can be (FIG. 7b) or is (FIG. 7c) pressed into the cavity 17 of the head 13 of the rod 11 by means of an insert 57. In order to attain the widening, the end 21 of the band 23 is brushed upward by means of a brushing tool 59 (FIG. 7a).

To press in, the insert 57, which is designed as a ring insert in FIG. 7, is threaded onto the band 23 and introduced into the cavity 17 of the head 13 so that the individual fibers, which project radially in all directions toward the introduction direction 25, are clamped between the front side of the ring insert 57 and the limit of the cavity 17. In order to increase the holding forces of such a connection between the band 23 and the rod 11, a centrally positioned spike 61, which protrudes into the cavity 17 against the introduction direction 25, and a lug 63, which runs around the spike 61 with the lug also protruding into the cavity 17 against the introduction direction 25, can be provided (FIG. 7d).

In accordance with an undepicted eighth embodiment of the invention, the end of the band that can be introduced into the cavity is cemented, particularly by means of glue or cement. In this way, the fibers of the band are joined with one another so that the sliding of the individual fibers against one another is prevented and thus it is possible to attain a greater holding force for the connection between the band and the rod.

In accordance with an undepicted ninth embodiment of the invention, the end of the band that can be introduced or is introduced into the cavity is a formed through melting, shaping, and subsequent hardening. In particular, the shape can be such that the end of the band is designed as a hook after curing.

FIG. 8 shows a stabilization system according to a tenth embodiment of the invention, in which the band-fastening comprises a separate component 65, wherein the rod 11 is, or can be fastened to the band-fastening—that is, in particular, on the separate component 65 and also on a common pedicle screw 67. In particular, the separate component 65 is not, or cannot be, fastened directly on the common pedicle screw 67.

FIGS. 8a and 8b show a stabilization system when implanted. The rod 11 connects two pedicle screws 67, 69, which comprise the common pedicle screw 67 and are each fastened on a vertebra of a vertebral column to form a rigid stiffening system. The band 23, which is prestressed when pulled, connects three pedicle screws 67, 71, 73, which comprise the common pedicle screw 67, wherein the pedicle screws 71, 73 are also each fastened to a vertebra to form an elastic support system. Compressed pressure bodies 75, 77 are located between the pedicle screws 67 and 71 and between the pedicle screws 71 and 73; they completely surround the band 23 in the circumferential direction. The common pedicle screw 67 is correlated with the stiffening system and also the support system.

The band 23 and the rod 11 are connected with one another by the separate component 65. The separate component 65 extends essentially perpendicular to the longitudinal extension of the band 23 or perpendicular to the longitudinal extension of the rod 11, which essentially run staggered parallel and medial/lateral with respect to one another, whereas, at least with the embodiments in accordance with FIGS. 1 to 7, the longitudinal extension of the band and the longitudinal extension of the rod run, at least without a medial/lateral staggering, parallel to one another. In accordance with FIG. 8, the separate component 65 can be located, relative to the common pedicle screw 67, both on the side of the support system (FIG. 8a) and also on the side of the stiffening system (FIG. 8b).

The embodiment example in accordance with FIG. 8c shows a separate component 65 that has two tube-like passages 79, 81 for the fastening of the band 23 and for the fastening of the rod 11. The passage 79 to the fastening of the rod 11 has an upper and a lower half-shell 83, 85, which can be moved relative to one another by means of a holding screw 87 in order to clamp the rod 11. Perpendicular to the passage 81 for the fastening of the band 23, there is an opening 89 into which a pressure element 91, for example, a clamping screw for the clamping of the band 23, can be inserted or is inserted on the common pedicle screw 67.

The separate component 65 can be constructed in several parts, wherein, in particular, different relative positions of the parts of the separate component 65 can be implemented relative to one another. Such a component 65 is shown in the embodiment examples according to FIGS. 8d, 8e, and 8f. The separate component 65 has a tube-like access or passage 81 for the band 23, which can be fastened by means of the clamping screw 91 introduced through the opening 89. The rod 11, which can be introduced in the sector-wise open passage 79 when implanted, can also be fastened to the separate component 65 analogous to band 23 by means of a clamping screw 93 introduced through an opening 95. The separate component 65 in which the passage is formed is provided with a rotating axle 97 between the one part of the separate component 65 in which the access or passage 81 is formed, and the other part of the separate component 65 in which the passage 79 is formed, so that the parts of the separate component 65 can be rotated relative to one another. An adjusted relative position of the two parts relative to one another can be locked by means of a locking screw 99.

Other embodiment examples of the separate component 65 are shown in FIGS. 8g and 8h, either in perspective (FIG. 8g) or in a top or transverse view (FIG. 8h). In particular, it is clear that, in an angularly constructed one-part separate component 65 or a multipart, separate component 65, the distance of the parts of the separate component 65 relative to one another can be changed by linear displacement.

The embodiment example according to 8i shows a separate component 65, into which, an undepicted rod can be introduced from one side and an undepicted band from the other, opposite side. The separate component 65, which, to a certain extent is designed as a double sleeve, has two tube-like accesses 79, 81. Furthermore, openings 89, 95 are provided in order to connect the rod and the band with the separate component 65 by means of undepicted clamping screws.

FIG. 9 shows a stabilization system in accordance with an eleventh embodiment of the invention in which the band-fastening comprises a separate component 65, wherein an undepicted rod is, or can be fastened onto the band-fastening 65, and the band-fastening 65 to an undepicted common pedicle screw. In particular, the rod is not, or cannot be, fastened directly to the common pedicle screw.

In the embodiment example according to FIGS. 9a and 9b, the separate component 65 has a central passage 101 provided for the fastening of the separate component 65 to the common pedicle screw. Furthermore, two passages or accesses 79, 81, running perpendicular to the central passage 101 and parallel to one another in the separate component 65, are designed for the fastening of the band and the rod. For the clamping of the band, an opening 89 is provided into which an undepicted clamping screw can be inserted. The passage 79 is slit and can be constricted by means of the common pedicle screw so that the rod can be effectively clamped.

FIG. 10 shows a stabilization system according to a twelfth embodiment of the invention, in which the band-fastening comprises a separate component 65, wherein the band-fastening and the rod are, or can be fastened to the common pedicle screw 67. In particular, the rod 11 is not, or cannot be, fastened directly to the separate component 65.

The separate component 65 according to FIG. 10a has a sleeve or an access for fastening band 23 and a fastening ring 103 for fastening to the common pedicle screw 67, wherein the longitudinal axis of the sleeve 81 and the middle axis of the fastening ring 103 are essentially perpendicular to one another. The fastening ring 103 can also have a recess 105 for the rod 11 (FIG. 10b).

FIG. 11 shows a stabilization system according to a thirteenth embodiment of the invention, in which the band-fastening comprises the common pedicle screw 67, wherein the rod 11 can be fastened, or is fastened, to a separate component 107, which is, or can be fastened to the common pedicle screw 67. In particular, the rod 11 is not, or cannot be, fastened to the common pedicle screw 67.

The separate component 107 according to FIG. 11 has two laterally placed click arms 109 with which the separate component 107 is, or can be fastened according to a type of click closure to the common pedicle screw 67. The click arms 109 lock into lateral depressions 111 of the common pedicle screw 67 for fastening. Moreover, the separate component 107 has an undepicted access into which the rod 11 is, or can be introduced and an opening 95 into which an undepicted clamping screw for the fastening of the rod 11 can be introduced. Moreover, an opening 113 is provided through which an undepicted fastening screw for the additional fastening of the separate component 107 to the common pedicle screw 67 can be introduced or is introduced.

FIG. 12 shows a stabilization system according to a fourteenth embodiment of the invention, in which the band-fastening comprises the common pedicle screw 67, wherein the rod 11 is, or can be fastened to the common pedicle screw 67 by means of a crossbar 115 which, when implanted, is essentially perpendicular to the longitudinal extension of the band 23.

The stabilization system depicted in FIG. 12 shows a stiffening system, followed on its two ends by a support system—that is, two common pedicle screws 67 and two crossbars 115 are present. The crossbars 115, shaped essentially in the form of an S, can have a passage 79, which is open sector-wise on their end, correlated with the rod 11, or a passage 79, which is closed in the circumferential direction. To fasten a crossbar 115 on a common pedicle screw 67, a longish hole 117 is formed on the end correlated with the common pedicle screw 67 so that various relative positions are possible between the common pedicle screw 67 and the rod 11. The longitudinal extension of the rod 11 and the longitudinal extension of the band 23 run parallel and staggered medially/laterally relative to one another.

Figure 13:
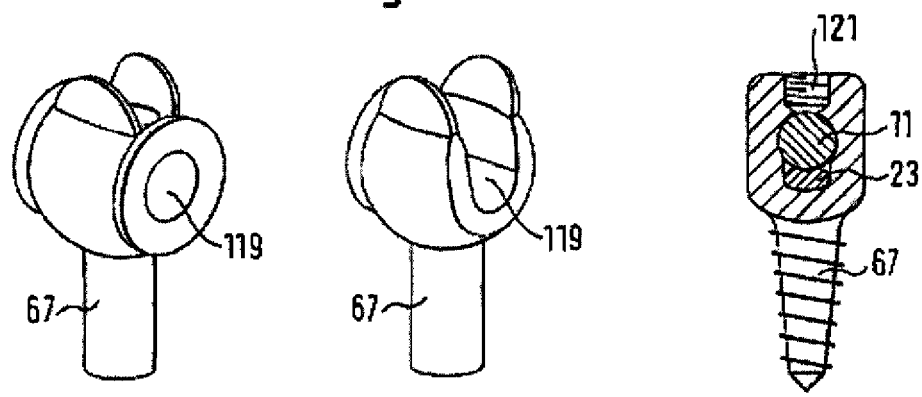

FIG. 13 shows a stabilization system according to a fifteenth embodiment of the invention, in which the band-fastening comprises the common pedicle screw 67, wherein the rod 11 is, or can be fastened to the common pedicle screw 67 and the common pedicle screw 67 has a common passage 119 for the band 23 and the rod 11.

In the embodiment example according to FIG. 13, the band 23 and the rod 11 are located next to one another or above one another within the common passage 119 of the common pedicle screw 67. The band 23 and the rod 11 are jointly compressed by means of an undepicted clamping screw which is, or can be introduced through an opening 121 formed in the common pedicle screw 67 so that both the band and also the rod 11 are effectively clamped.

FIG. 14 shows a stabilization system according to a sixteenth embodiment of the invention. Analogous to the embodiment according to FIG. 13, the embodiment according to FIG. 14 has a common passage 119 for the band 23 and the rod 11 and an opening 121 to introduce a clamping screw.

Figure 14A:
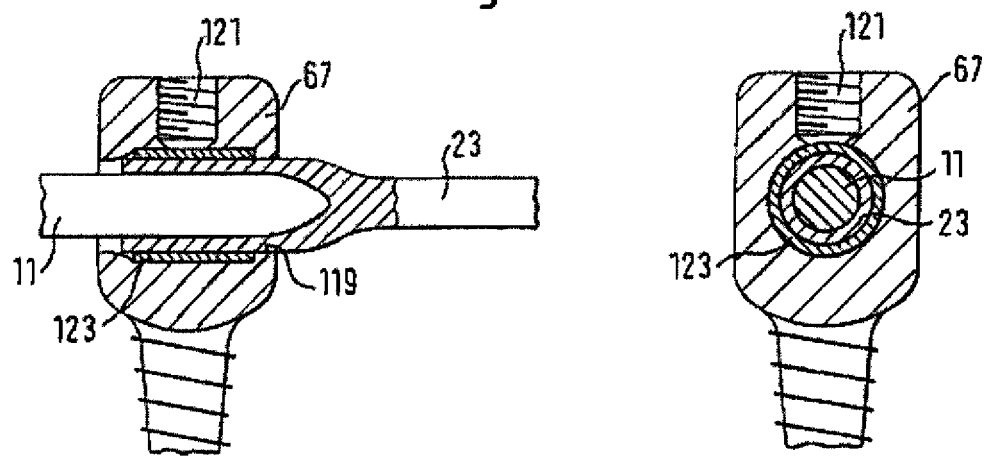
Figure 14B:
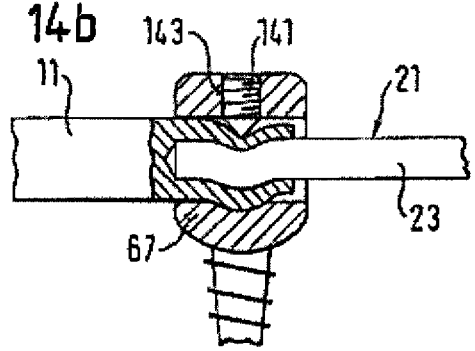

In the embodiment example according to FIG. 14a, the band 23 is, or can be pulled over the rod 11, in contrast to the embodiment according to FIG. 13. Moreover, a sleeve 123 is, or can be shoved into the common passage 119 that in turn again surrounds the band 23. Otherwise, the band 23 and the rod 11 can be clamped analogous to the embodiment in FIG. 13. An embodiment example is shown in FIG. 14b in which the end 21 of the band 23 is, or can be introduced into rod 11, similar to what is shown in FIGS. 1 to 7, wherein by means of a clamping screw 141, which is, or can be introduced into the common pedicle screw 67 through an opening 143, the band 23 and the rod 11 can be clamped in.

Figure 14C:
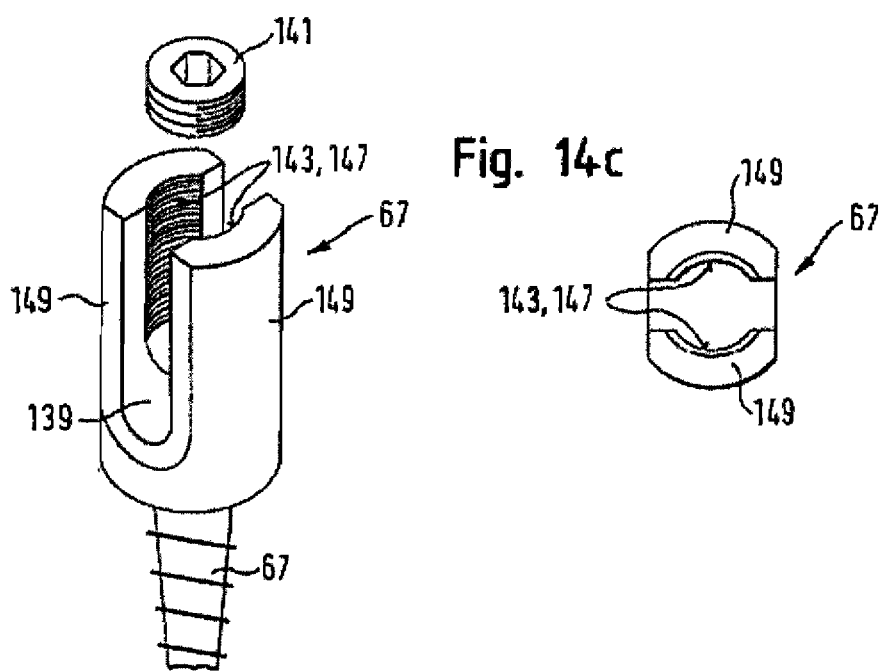
Figure 14D:
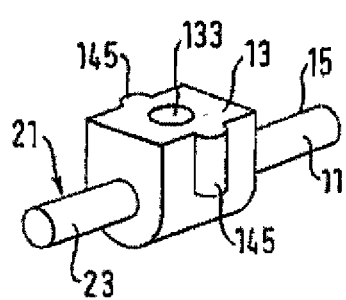
Figure 14E:
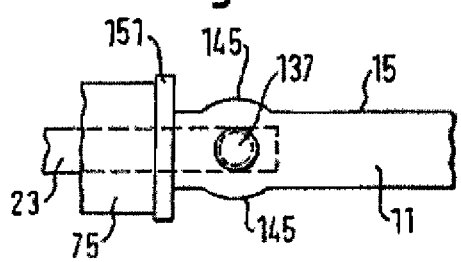
Figure 14F:
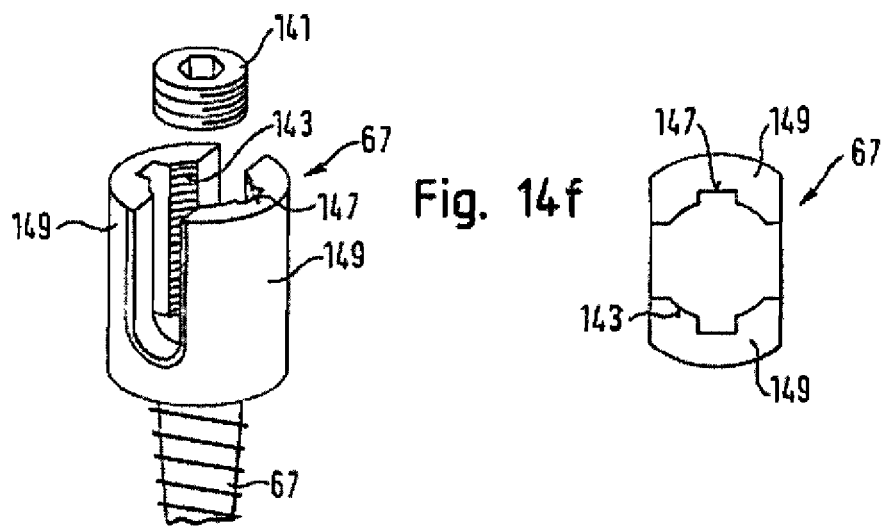
Figure 14G:
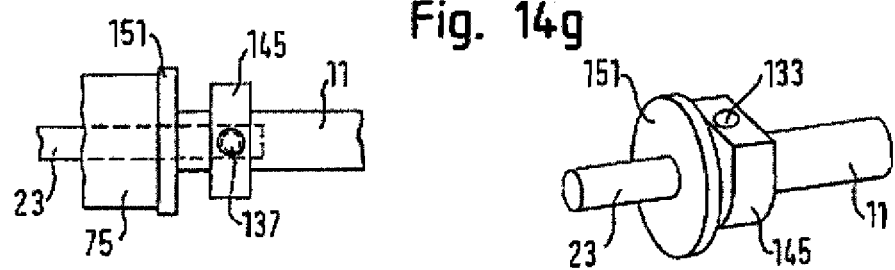
Figure 14H:
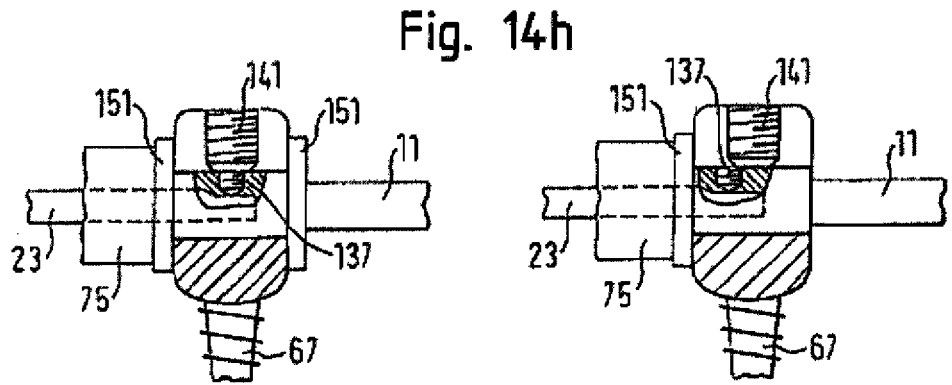

In the embodiment example in accordance with FIG. 14c, the common pedicle screw 67 is designed as a tuning fork on its upper end, so that a recess 139 is formed between two prongs 149 into which a rod is, or can be laid. The mounting of the rod on the common pedicle screw 67 takes place by means of a clamping screw 141 that is, or can be inserted into the bore sections 143 of the two prongs 149, wherein the bore sections have an internal thread. The end 13 of the rod 11, which is designed for connection with the end 21 of the band 23, can have a diameter larger than that of a middle part 15 of the rod 11 (FIG. 14d). The band 23 is, or can be connected with the rod 11 by means of a clamping screw 137 that is, or can be introduced through an opening 133 into the rod 11.

To guide the rod 11 in the assembly with the common pedicle screw 67 or for the correct positioning of the rod 11 with regard to the common pedicle screw 67, guiding means, for example, one or more round or angular pegs 145 are formed on the head 13 of the rod 11 (FIGS. 14d, 14e, 14g) that mesh into guiding means of the common pedicle screw 67 (FIGS. 14c, 14f), for example, one or more recesses, slots, or grooves 147, which, in particular, correspond to the bore sections 143 of the two prongs 149 (FIG. 14c).

Moreover, at least one, particularly plate-shaped, flange 151 oriented perpendicular to the longitudinal axis of the rod 11 can be provided (FIGS. 14e, 14g, 14h) that is connected with the rod 11 and permits correct positioning of the rod 11 with regard to the common pedicle screw 67 or offers a guide when the stabilization system is assembled. If the flange 151 is designed as a closure of the end 13 of the rod 11, the flange can also be used simultaneously as a stop 151 for a pressure body 75 of a support system of the stabilization system.

Figure 15:
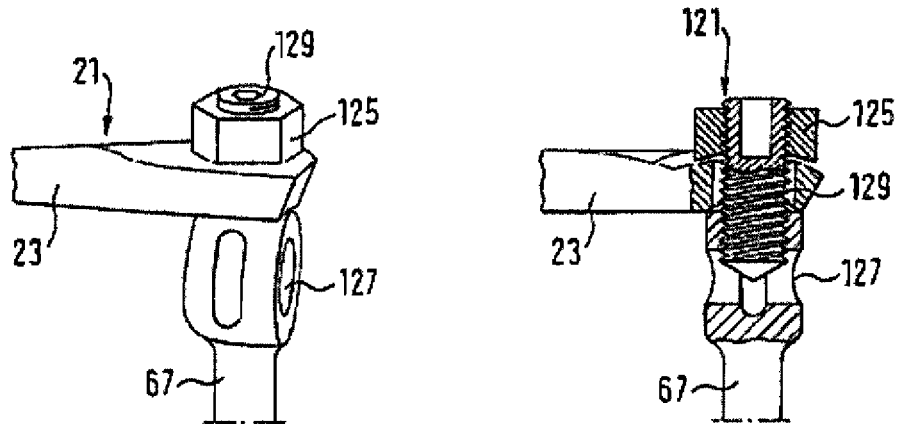

FIG. 15 shows a stabilization system in accordance with a seventeenth embodiment of the invention, in which the band-fastening comprises the common pedicle screw 67, wherein an undepicted rod is, or can be fastened to the common pedicle screw 67 and the band 23 is, or can be clamped between the pressure mechanism, in particular, a nut 125, and the common pedicle screw 67, wherein the common pedicle screw 67 has a passage 127 for the rod.

The rod introduced into the passage 127 is effectively clamped by means of a threaded pin 129 that has a continuous external thread and which is, or can be introduced through an opening 121 into the common pedicle screw 67. The nut 125 is placed on the end of the threaded pin 129 that projects from the common pedicle screw 67 in order to clamp the band 23 between the common pedicle screw 67 and the nut 125. For this purpose, the end 21 of the band 23 to be clamped is made as a loop into which the threaded pin 129 meshes.

Reference Symbol List

11 Rod
13 Head
15 Middle part
17 Cavity
19 Band entry opening
21 End
23 Band
25 Introduction direction
27 Clamping sleeve
29 Protrusion
31 Clamping sleeve
33 Clamping rod
35 Opening
37 Hollow
39 Introduction aid
41 Clamping rod
43 Clamping rod
45 Projection
47 Press ring
49, 49' Ring, tapered ring
51 Inlay
53 Head
55 Shaft
57 Insert
59 Brush tool
61 Spike
63 Lug
65 Separate component
67 Common pedicle screw
69 Pedicle screw
71 Pedicle screw
73 Pedicle screw
75 Pressure body
77 Pressure body
79 Passage, access
81 Passage, access, sleeve
83 Upper half-shell
85 Lower half-shell
87 Holding screw
89 Opening
91 Clamping screw
93 Clamping screw
95 Opening
97 Rotating axle
99 Locking screw
101 Central passage
103 Fastening ring
105 Recess
107 Separate component
109 Click arm
111 Depression 113 Opening
115 Crossbar
117 Longish hole
119 Common passage
121 Opening
123 Sleeve
125 Nut
127 Passage
129 Threaded rod
131 Punch
133 Opening
135 Band exit opening
137 Clamping screw
139 Recess
141 Clamping screw
143 Opening, bore sections
145 Peg
147 Recess
149 Prong
151 Flange, stop

The invention claimed is:

1. An intervertebral stabilization system comprising:
a first vertebral fastener configured to be secured to a first vertebra;
a second vertebral fastener configured to be secured to a second vertebra;
a third vertebral fastener configured to be secured to a third vertebra;
a rigid member extending continuously from the first vertebral fastener to the second vertebral fastener and secured to each of the first vertebral fastener and the second vertebral fastener, the rigid member configured to provide rigid support between the first vertebra and the second vertebra of a spinal column, the rigid member including an end region having an opening extending therein, wherein the end region of the rigid member includes a first flange positionable on a first side of the second vertebral fastener and a second flange positionable on a second side of the second vertebral fastener, wherein the first and second flanges are integral with the rigid member;
an elastic support system positioned between the second vertebral fastener and the third vertebral fastener, the elastic support system configured to provide dynamic support between the second vertebra and the third vertebra of the spinal column including a spacer and a flexible member sized to insert into the spacer; and
a clamping member;
wherein an end portion of the flexible member extends into the opening of the rigid member and is clamped in the opening of the rigid member with the clamping member.

2. The intervertebral stabilization system of claim 1, wherein the clamping member comprises a clamping sleeve.

3. The intervertebral stabilization system of claim 2, wherein the clamping sleeve is disposed about the end portion of the flexible member and at least a portion is disposed within the opening of the rigid member.

4. The intervertebral stabilization system of claim 1, wherein the clamping member comprises a clamping pin.

5. The intervertebral stabilization system of claim 4, wherein the clamping pin extends through a portion of the rigid member and into the opening and engages the flexible member.

6. The intervertebral stabilization system of claim 1, wherein the clamping member comprises a clamping screw.

7. The intervertebral stabilization system of claim 6, wherein the clamping screw extends through a portion of the rigid member and into the opening and engages the flexible member.

8. The intervertebral stabilization system of claim 1, wherein the clamping member is a press ring disposed around the end region of the rigid member configured to secure the end portion of the flexible member in the opening.

9. The intervertebral stabilization system of claim 8, wherein a portion of the end region of the rigid member is displaced radially inward into contact with the flexible member, thereby constricting the opening around the flexible member.

10. The intervertebral stabilization system of claim 8, wherein a portion of the end region of the rigid member protrudes into the flexible member.

11. The intervertebral stabilization system of claim 8, wherein the press ring has an outside diameter greater than an outside diameter of the end region adjacent to the press ring.

12. The intervertebral stabilization system of claim 1, wherein the clamping member is an insert, and wherein the flexible member includes a plurality of individual filaments;
wherein the insert is positioned in the opening such that the plurality of individual filaments are clamped between an inner surface of the opening and a surface of the insert.

13. The intervertebral stabilization system of claim 12, wherein the insert is a ring insert disposed around the flexible member.

14. The intervertebral stabilization system of claim 12, wherein the insert is an inlay extending into an end of the flexible member.

15. The intervertebral stabilization system of claim 1, wherein the spacer is a pressure member.

16. The intervertebral stabilization system of claim 1, wherein the end region of the rigid member includes a medial portion between the first flange and the second flange, wherein the medial portion is positionable within a channel of a head portion of the second vertebral fastener.

17. The intervertebral stabilization system of claim 1, wherein the second vertebral fastener is a pedicle screw including a threaded shaft portion and a head defining a channel, wherein at least a portion of the opening of the rigid member is positionable in the channel of the pedicle screw.

18. The intervertebral stabilization system of claim 1, wherein the rigid member includes a flange, wherein the spacer is positionable in abutment with the flange of the rigid member.

19. The intervertebral stabilization system of claim 18, wherein the flange is configured to space the spacer from the second vertebral fastener.

20. The intervertebral stabilization system of claim 1, wherein the rigid member has a longitudinal axis, wherein the opening is offset from the longitudinal axis of the rigid member.

21. The intervertebral stabilization system of claim 1, wherein the end portion of the flexible member is coaxial with the end region of the rigid member.

22. The intervertebral stabilization system of claim 1, wherein the end region of the rigid member has a larger diameter than a central region of the rigid member.

* * * * *